US00PP24427P3

(12) United States Plant Patent
Schoone

(10) Patent No.: US PP24,427 P3
(45) Date of Patent: May 6, 2014

(54) ***PHALAENOPSIS* ORCHID PLANT NAMED 'MONTECITO'**

(50) Latin Name: ***Phalaenopsis* hybrid**
Varietal Denomination: Montecito

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 256 days.

(21) Appl. No.: 13/067,029

(22) Filed: May 3, 2011

(65) Prior Publication Data

US 2012/0102606 P1 Apr. 26, 2012

(30) Foreign Application Priority Data

Oct. 20, 2010 (NL) ..... PBR OPS730

(51) Int. Cl.
*A01H 5/00* (2006.01)

(52) U.S. Cl.
USPC ..... Plt./311

(58) Field of Classification Search
USPC ..... Plt./311
See application file for complete search history.

(56) References Cited

U.S. PATENT DOCUMENTS

PP14,266 P3 * 11/2003 van Rijsselberghe ..... Plt./311
PP22,090 P3 * 8/2011 Pen-chih ..... Plt./311

OTHER PUBLICATIONS

The Santa Barbara Orchid Estate, Orchid of the Day, Jan. 21, 2013, for *Cymbidium schroederi* 'Montecito' retrieved from the internet at <http://www.sborchid.com/cyms-standard.php?range=s> , retrieved Mar. 4, 2013, five pages.*

* cited by examiner

*Primary Examiner* — June Hwu
*Assistant Examiner* — Louanne Krawczewicz Myers
(74) *Attorney, Agent, or Firm* — Foley & Lardner LLP

(57) ABSTRACT

A new and distinct *Phalaenopsis* plant named 'Montecito' particularly characterized by flowers which are white, within the labellum there is yellow and some purple/red; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Montecito'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Montecito'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Montecito' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Montecito' originated from a cross made by the inventor in 1998 in Strengweg, Heemskerk, The Netherlands. The female or seed parent is the *Phalaenopsis* cultivar designated 'White Castle', unpatented. The male or pollen parent is the *Phalaenopsis* cultivar designated 'Moon World', unpatented. The new *Phalaenopsis* 'Montecito' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in January, 2006 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Montecito', which in combination distinguish this *Phalaenopsis* as a new and distinct cultivar:

1. flowers which are white, within the labellum there is yellow and some purple/red;
2. plant produces more than one inflorescence;
3. plants may be propagated economically and uniformly using tissue culture;
4. inflorescence is long and sturdy; and
5. relatively short, dark-green foliage.

In comparison with the parental cultivars of 'Montecito', the female parent 'White Castle' has large white flowers (about 12 cm) and the male parent 'Moon World' has flowers which are about 9 cm in size, whereas the flowers of 'Montecito' are about 10.5 cm in size.

The most similar commercial varieties to the claimed variety are the parent varieties, 'White Castle' and 'Moon World', to which a comparison is provided above.

BRIEF DESCRIPTION OF THE PHOTOGRAPHS

The accompanying photographs illustrate the overall appearance of the new *Phalaenopsis* 'Montecito' showing the colors as true as is reasonably possible with colored reproductions of this type. Colors in the photographs may differ slightly from the color values cited in the detailed botanical description, which accurately describe the color of 'Montecito'.

DETAILED BOTANICAL DESCRIPTION

Figure 1:
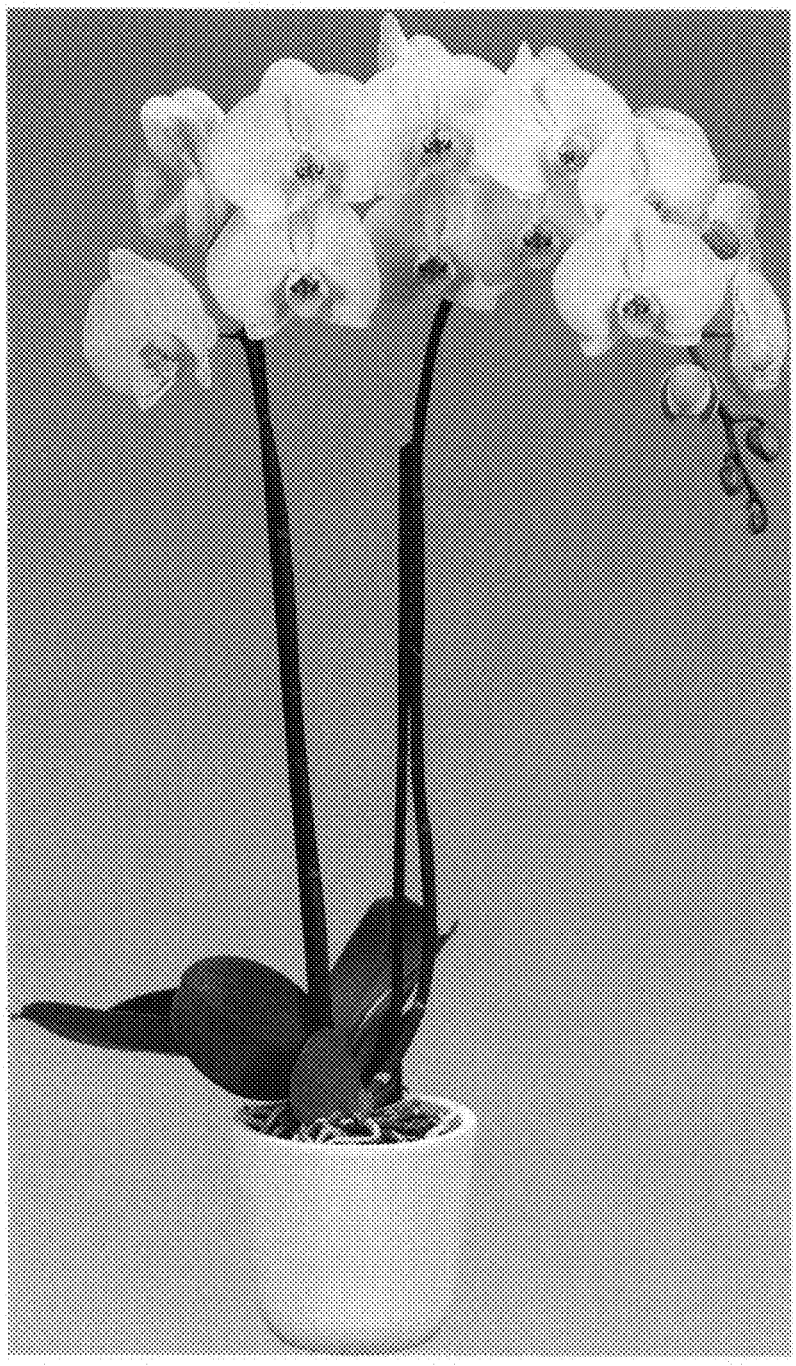
FIG. 1 shows a side view perspective of a typical flowering plant of 'Montecito' in a 12 cm pot, at 16 months of age.

The new *Phalaenopsis* cultivar 'Montecito' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Montecito' as grown in a greenhouse in Strengweg, Heemskerk, The Netherlands, under conditions which closely approximate those generally used in commercial practice. Initially, the ideal temperature to grow plants of 'Montecito' is 27° C. during the day and at night. Then, during the flowering phase of 'Montecito', the ideal growing temperature is 20-22° C. during the day and 18° C. at night. Light levels for growing 'Montecito' are a minimum of 5,000 lux and a maximum of 10,000 lux. A balanced fertilizer with level of 200 ppm N, 87 ppm P, 168 ppm K is applied. Duration of growth of 'Montecito' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Montecito' plants described is 12 months after potting.

Classification:

*Botanical.*—*Phalaenopsis* hybrid.

Parentage:

*Female or seed parent.*—*Phalaenopsis* cultivar designated 'White Castle', unpatented.

*Male or pollen parent.*—*Phalaenopsis* cultivar designated 'Moon World', unpatented.

Propagation:

*Type.*—Tissue culture.

*Rooting habit and description.*—Fleshy; approximately 5 mm-9 mm wide and green in color (RHS 137B); freely branching. It takes 12 weeks for plants growing in tissue culture to initiate roots Plant:

*Size at maturity.*—Height (from bottom of pot to the top of the highest flower): about 73 cm. Spread: about 35 cm.

*Growth habit.*—Standard; dark-green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 5 to 8 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—None.

*Mature leaf length.*—About 16 cm and 20 cm.

*Mature leaf width.*—About 7 cm and 9 cm.

*Mature leaf thickness.*—About 1.5 mm.

*Mature leaf color.*—Upper side: RHS 137A. Under side: RHS 137C.

*Leaf base.*—Acute.

*Margin.*—Entire.

*Venation.*—Pattern: parallel. Color of midvein: upper side: green (RHS 137A). Under side: green (RHS 137C).

Raceme:

*Quantity per plant.*—About 1 to 2.

*Number of flowers per raceme.*—About 8 to 10.

*Length.*—About 55 cm to 80 cm.

*Diameter.*—About 6 mm to 9 mm.

*Strength.*—Strong.

*Aspect.*—Upright.

*Texture.*—Glabrous and smooth.

*Color.*—Green (RHS 137A) with some RHS 137D.

*Internode.*—Length: about 35 mm to 45 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 to 25 mm. Diameter (at midpoint): about 13 to 20 mm. Shape: egg-shaped/oval. Color: yellow-green (RHS 145B).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
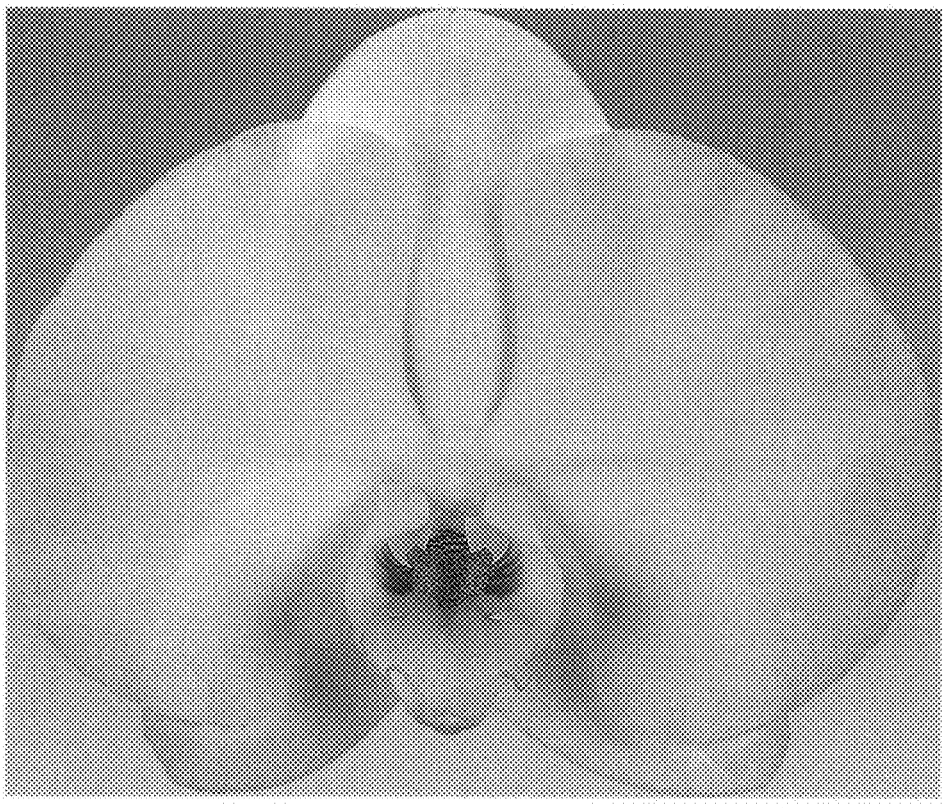
FIG. 2 shows a close-up view of the typical buds and flowers of 'Montecito'.
Figure 3:
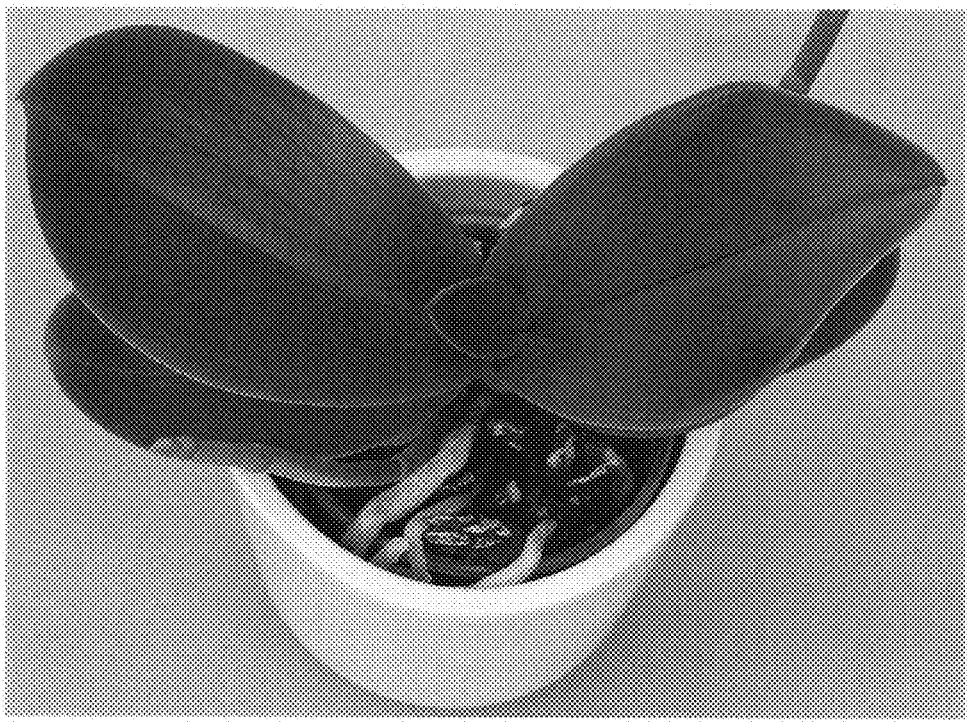
FIG. 3 shows a close-up view of the typical leaves of 'Montecito'.

*Flower.*—Rate of opening: Flowers fully opened about 2 to 3 days after petal and sepal separation. Orientation at opening: slanted upward and outward. Shape: Typical shape of *phalaenopsis* orchid; see FIG. 2. Size: Height: about 80 mm. Diameter: about 105 mm. Depth of tube: about 15 mm.

*Petals.*—Quantity and arrangement: three petals and three sepals that are trimerous, overlapping and arranged in 2 whorls. Petals are more pronounced than sepals. Arrangement: Inner whorl of petals comprises 3 petals: 2 lateral petals and labellum. 2 lateral petals: Overall shape: broadly ovate and weakly cupped. Apex: oval. Margin: weakly undulate. Length: about 64 mm. Width: about 45 mm. Texture: Upper surface: smooth and satiny. Under surface: smooth and satiny. Color (when fully opened): upper side: white (RHS NN155C); Under side: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: oval. Length: about 18 mm. Width (not flattened): about 23 mm. Texture: Upper & under surface: smooth and satiny. Color (when fully opened): Main color is white (RHS NN155C). Upper side: lateral lobes: at the base there are purple/red stripes (RHS 64A) and the bottom edges (to the corners) are yellow (RHS 12A). Midlobe: At the base, in the center and in the upper corners yellow (RHS 12A). In between only a yellow haze. Under side: Midlobe: at the base and on the upper edges yellow (RHS 12C). Lateral lobes: some yellow at the bottom edges (RHS 12C). Cirrhi: long (about 19 mm) and curly. Color: white (RHS NN155C) with yellow from halfway to the tips (RHS 12A). Pestle (Callosities): Length: about 8 mm. Width (not flattened): about 6 mm. Color: yellow on the sides and on top (RHS 12A) with purple/red spots and stripes (RHS 64A).

*Sepals.*—Arrangement: Outer whorl of the flower comprises 3 sepals. Overall shape: elliptical and weakly cupped. Margin: entire and weakly undulate. Length: about 49 mm. Width: about 30 to 36 mm. Apex: Dorsal is round. Lateral is more oval. Base: Acute. Texture: Upper & under surface: smooth and satiny. Color (when fully opened): upper & under surface: white (RHS NN155C).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 10 mm. Diameter: about 7 mm. Color: white RHS NN155C.

*Pollinia.*—Quantity: Two. Diameter: about 1 mm. Color: orange RHS 25A.

*Ovary.*—Length: about 6 mm. Diameter: about 7 mm. Color: white (RHS NN155C).

*Pedicel.*—Length: about 45 to 60 mm. Diameter: about 4 mm. Texture: glabrous and smooth. Color: yellow/green (RHS 145A runs into RHS 145B which runs into RHS 145D). Near the flower a haze of purple visible (RHS N78B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Montecito', as illustrated and described herein.

* * * * *